United States Patent
Jackson et al.

(10) Patent No.: US 10,496,742 B2
(45) Date of Patent: Dec. 3, 2019

(54) SYSTEM FOR AND METHOD OF EVALUATING MEDICAL IMAGES IN A NETWORKED COMPUTER ENVIRONMENT

(71) Applicant: Proscia Inc., Haverford, PA (US)

(72) Inventors: Brian H. Jackson, Poquoson, VA (US); Coleman C. Stavish, Havertown, PA (US)

(73) Assignee: PROSCIA INC., Haverford, PA (US)

( * ) Notice: Subject to any disclaimer, the term of this patent is extended or adjusted under 35 U.S.C. 154(b) by 208 days.

(21) Appl. No.: 15/611,930

(22) Filed: Jun. 2, 2017

(65) Prior Publication Data

US 2018/0349554 A1    Dec. 6, 2018

(51) Int. Cl.
| | | |
|---|---|---|
| *G06F 17/24* | (2006.01) | |
| *G16H 30/20* | (2018.01) | |
| *G16H 30/40* | (2018.01) | |
| *G06T 7/00* | (2017.01) | |
| *G16H 10/40* | (2018.01) | |

(52) U.S. Cl.
CPC .......... *G06F 17/248* (2013.01); *G06F 17/243* (2013.01); *G06T 7/0012* (2013.01); *G16H 10/40* (2018.01); *G16H 30/20* (2018.01); *G16H 30/40* (2018.01)

(58) Field of Classification Search
CPC ....... G06F 17/248; G16H 30/20; G16H 30/40
See application file for complete search history.

(56) References Cited

U.S. PATENT DOCUMENTS

| | | | | |
|---|---|---|---|---|
| 7,738,688 B2 * | 6/2010 | Eichhorn | ............... | G02B 21/26 382/133 |
| 2011/0022658 A1 * | 1/2011 | Pace | ...................... | G06Q 10/10 709/204 |
| 2011/0060766 A1 * | 3/2011 | Ehlke | .................... | G06F 3/0481 707/802 |
| 2011/0274320 A1 * | 11/2011 | Pace | ....................... | H04L 67/10 382/128 |
| 2015/0003716 A1 * | 1/2015 | Lloyd | ................... | G06F 19/321 382/133 |
| 2017/0193657 A1 * | 7/2017 | Madabhushi | ............ | G06N 3/08 |

* cited by examiner

*Primary Examiner* — Nay A Maung
*Assistant Examiner* — Jose Torres
(74) *Attorney, Agent, or Firm* — MH2 Technology Law Group LLP

(57) ABSTRACT

The present disclosure generally relates to evaluating medical images. Some embodiments access stored medical images, provide a form template construction application to a coordinating user, and provide review applications to reviewing users. The form template construction application provides a tool for creating on a form template at least one user control for designating a region on a medical image and a tool for creating on a form template at least one user input for receiving diagnosis data about a medical image. The form template construction application distributes review forms based on the form template to the reviewing users. The reviewing users provide review data for each image, such an identification of a region and a corresponding diagnosis. A central server collects the review data from the reviewing users and stores it for use by the coordinating user.

20 Claims, 7 Drawing Sheets

SYSTEM FOR AND METHOD OF EVALUATING MEDICAL IMAGES IN A NETWORKED COMPUTER ENVIRONMENT

FIELD

This disclosure relates generally to obtaining characterizations of medical images or portions thereof.

BACKGROUND

A common task for both medical researchers and practicing physicians is to have experts identify certain types of phenomena (e.g., location and characteristics of a tumor) in a whole-slide medical image. Currently, such expert review is obtained by providing an expert with a physical medical whole-slide image sent via courier. The expert may generate notes about the image using, e.g., a word processor entirely unconnected with the image, and send the notes to the requesting researcher or physician by regular mail, for example. This existing review process is slow and requires extensive manual human intervention.

SUMMARY

According to some embodiments, a computer-implemented method of evaluating medical images is presented. The method includes accessing an electronically stored plurality of medical images; providing to a computer of a coordinating user, by a server computer and over a computer network, a form template construction application, the form template construction application including a tool for creating on a form template at least one user control for designating a region on a medical image of the plurality of medical images, and a tool for creating on a form template at least one user input for receiving diagnosis data about a medical image of the plurality of medical images; receiving electronically at the server computer, from the computer of the coordinating user, form template construction inputs provided to the form template construction application by the coordinating user, the form template construction inputs including data representing at least one user control for designating a region on a medical image of the plurality of medical images, and data representing at least one user input for receiving diagnosis data about a medical image of the plurality of medical images; creating an electronic form template based on the form template construction inputs, the electronic form template specifying at least one user control for designating a region on a medical image of the plurality of medical images, and at least one user input for receiving diagnosis data about a medical image of the plurality of medical images; receiving electronically at the server computer, from the computer of the coordinating user, data representing a list of reviewing users; sending electronically over the computer network and by a server computer, to a computer of at least one reviewing user whose identity is on the list of reviewing users, an invitation to review the plurality of medical images; receiving an affirmative response to the invitation from the computer of the at least one reviewing user; providing electronically, by a server computer and over the computer network, a review application to the computer of the at least one reviewing user; providing electronically, by a server computer and over the computer network, to an executing instance of the review application on the computer of the at least one reviewing user, the form template and the plurality of medical images; receiving electronically by a server computer over the computer network, from the computer of the at least one reviewing user, and through the review application, review data for each of the plurality of electronically stored medical images representing inputs by the at least one reviewing user to a plurality of review forms derived from the form template, the review data representing at least one specified region on a medical image of the plurality of medical images and at least one diagnosis datum for a medical image of the plurality of medical images; and electronically storing the review data in persistent memory.

Various optional features of the above embodiments include the following. The method may include training a machine learning component using the plurality of medical images and the review data; receiving a novel medical image; applying the machine learning component to the novel medical image; and obtaining a diagnosis for the novel medical image from the machine learning component. The method may include including applying stain normalization to the plurality of medical images prior to the training. The receiving electronically by a server computer over the computer network, from the computer of the at least one reviewing user, and through the review application, review data for each of the plurality of electronically stored medical images representing inputs by the at least one reviewing user to a plurality of review forms derived from the form template may include: receiving multiple instances of partial review data sent automatically from the review application without reviewing user initiation; and persisting each of the multiple instances of partial review data in persistent memory. The form template may specify a sequence of prompts, the sequence of prompts including image selection prompts and image metadata prompts; the image selection prompts may include the at least one user control for designating a region on a medical image of the plurality of medical images; and the image metadata prompts may include the at least one user input for receiving diagnosis data about a medical image of the plurality of medical images. Each prompt of the sequence of prompts may include an instruction for responding to the prompt. Each instruction may include a designation of one of: completion mandatory or completion optional. The at least one user control for designating a region on a medical image of the plurality of medical images may include at least one of: a shape selector, or a number of selectable regions ceiling; and the at least one user input for receiving diagnosis data about a medical image of the plurality of medical images may include at least one of: a freeform text input field, a Boolean input, a numeric input, or a multiple choice input. The plurality of medical images may include whole-slide medical images. The review application may be configured to display to the reviewing user each medical image of the plurality of medical images in sequence.

According to various embodiments, a system for evaluating medical images is presented. The system includes at least one server computer communicatively coupled to a computer network and to an electronically stored plurality of medical images, the at least one server computer configured to provide to a computer of a coordinating user a form template construction application, the form template construction application including a tool for creating on a form template at least one user control for designating a region on a medical image of the plurality of medical images, and a tool for creating on a form template at least one user input for receiving diagnosis data about a medical image of the plurality of medical images; where the at least one server computer is further configured to receive electronically, from the computer of the coordinating user, form template construction inputs provided to the form template construction application by the coordinating user, the form template construction inputs including data representing at least one user control for designating a region on a medical image of the plurality of medical images, and data representing at least one user input for receiving diagnosis data about a medical image of the plurality of medical images; where the at least one server computer is further configured to create an electronic form template based on the form template construction inputs, the electronic form template specifying at least one user control for designating a region on a medical image of the plurality of medical images, and at least one user input for receiving diagnosis data about a medical image of the plurality of medical images; where the at least one server computer is further configured to receive electronically, from the computer of the coordinating user, data representing a list of reviewing users; where the at least one server computer is further configured to send electronically over the computer network, to a computer of at least one reviewing user whose identity is on the list of reviewing users, an invitation to review the plurality of medical images; where the at least one server computer is further configured to receive an affirmative response to the invitation from the computer of the at least one reviewing user; where the server computer is further configured to provide electronically, over the computer network, a review application to the computer of the at least one reviewing user; where the at least one server computer is further configured to provide electronically, over the computer network, to an executing instance of the review application on the computer of the at least one reviewing user, the form template and the plurality of medical images; where the at least one server computer is further configured to receive electronically, over the computer network, from the computer of the at least one reviewing user, and through the review application, review data for each of the plurality of electronically stored medical images representing inputs by the at least one reviewing user to a plurality of review forms derived from the form template, the review data representing at least one specified region on a medical image of the plurality of medical images and at least one diagnosis datum for a medical image of the plurality of medical images; and where the at least one server computer is further configured to electronically storing the review data in persistent memory.

Various optional features of the above embodiments include the following. The system may include an electronic computer executing a machine learning component trained using the plurality of medical images and the review data, where the electronic computer is configured to receive a novel medical image, apply the machine learning component to the novel medical image, and provide a diagnosis for the novel medical image from the machine learning component. The electronic computer may be further configured to apply stain normalization to the plurality of medical images prior to training the machine learning component. The at least one server computer may be further configured to receive multiple instances of partial review data sent automatically from the review application without reviewing user initiation, and persist each of the multiple instances of partial review data in persistent memory. The form template may specify a sequence of prompts, the sequence of prompts including image selection prompts and image metadata prompts; the image selection prompts may include the at least one user control for designating a region on a medical image of the plurality of medical images; and where the image metadata prompts may include the at least one user input for receiving diagnosis data about a medical image of the plurality of medical images. Each prompt of the sequence of prompts may include an instruction for responding to the prompt. Each instruction may include a designation of one of: completion mandatory or completion optional. The at least one user control for designating a region on a medical image of the plurality of medical images may include at least one of: a shape selector, or a number of selectable regions ceiling; and the at least one user input for receiving diagnosis data about a medical image of the plurality of medical images may include at least one of: a freeform text input field, a Boolean input, a numeric input, or a multiple choice input. The plurality of medical images may include whole-slide medical images. The review application may be configured to display to the reviewing user each medical image of the plurality of medical images in sequence.

BRIEF DESCRIPTION OF THE DRAWINGS

Various features of the examples can be more fully appreciated, as the examples become better understood with reference to the following detailed description, when considered in connection with the accompanying figures, in which.

DESCRIPTION

Figure 1:
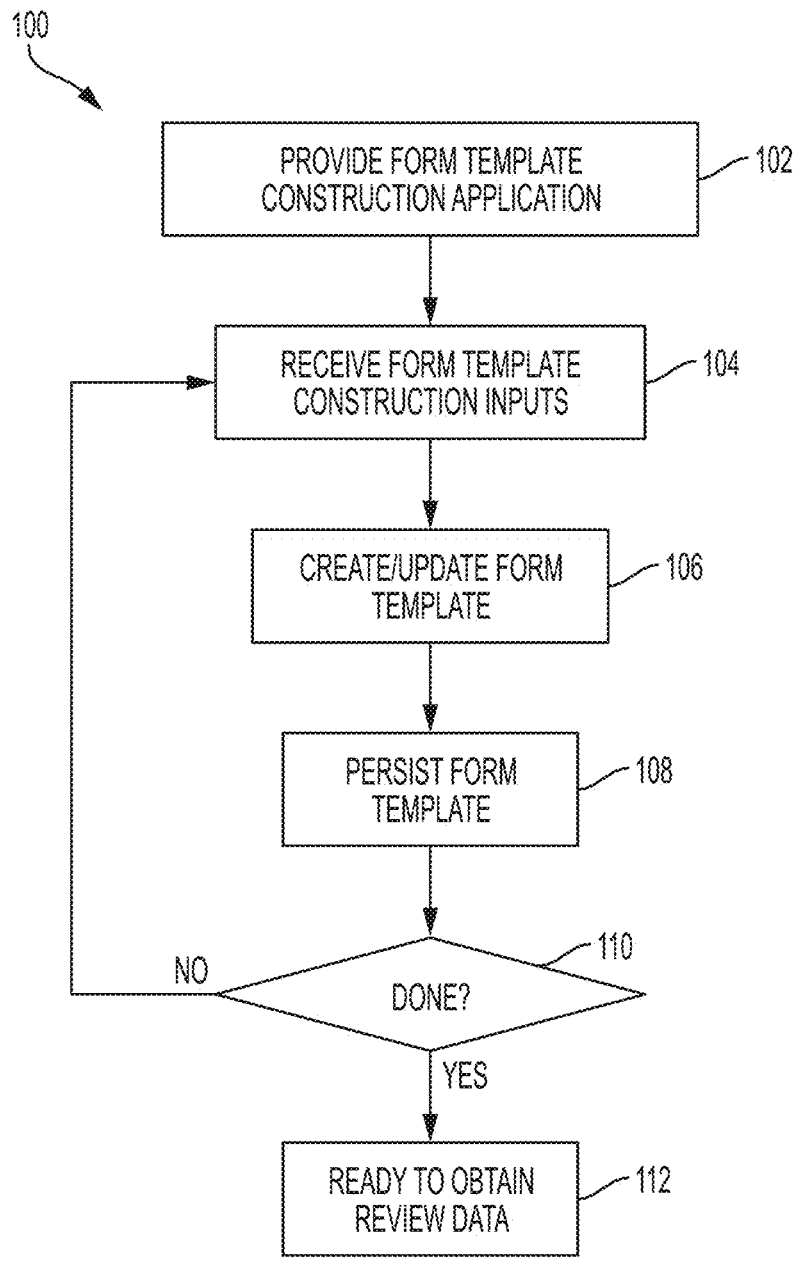
FIG. 1 is a flow diagram of a method for creating a medical image review form template according to some embodiments.

Reference will now be made in detail to the disclosed examples, which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific examples. These examples are described in sufficient detail to enable those skilled in the art to practice them and it is to be understood that other examples may be utilized and that changes may be made without departing from the scope of the disclosure. The following description is, therefore, merely exemplary.

The present disclosure provides systems for, and methods of, efficiently obtaining expert review data for medical images, in particular, whole-slide images. Some embodiments include two software applications: a form template construction application and a review application. These applications interact with a central server component to create and utilize an electronic reviewing environment for expert reviewers to provide their review data. As detailed below, in some embodiments, the central server provides the form template construction application to a coordinating user, who wishes to obtain review data for one or more medical images, and provides the review application to expert reviewers, who provide their expert review data. These and other features are detailed presently.

According to some embodiments, the form template construction application permits a coordinating user to create an electronic form template. In general, the coordinating user may be a medical researcher or practicing physician who wishes to obtain one or more expert reviews of one or more (typically many) medical images. The form template created by the coordinating user specifies the reviewer's tasks and sets forth software tools that the reviewer may use to annotate the images, for example. That is, the reviewing users provide their review data to electronic forms that are based on the form template created by the coordinating user.

According to some embodiments, expert reviewers, who may be remote from the coordinating user and each-other, obtain and execute the review application to accomplish their review. The expert reviewers may be medical professionals, for example. The review application, when executed, retrieves the medical images from a remote storage location, typically the central server, and sequentially displays them to the reviewing users. Thus, the review application provides the reviewing users with a forum in which they may access medical images and provide their corresponding review data. In particular, the review application obtains the review form template from the central server and uses it to generate the electronic forms into which the expert reviewers enter their review data. In more detail, the review application parses the form template and uses it to display a review form in which a respective medical image is displayed and in which the reviewers may enter comments or annotations. Thus, the review application allows reviewing users to provide comments and other review data using a form that is displayed within the application together with an image for review.

The review application and the obtained review data have a variety of uses. According to some embodiments, the review application may be used as an educational tool, allowing students or professionals to move through images and compare their own inputs against known values. This feature can allow for student test taking with digital image interaction that simulates tasks performed in a real work environment. According to some embodiments, the review data may be used as ground truth data for use within a machine learning algorithm. Such embodiments may utilize reviewing users to systematically input a ground truth for each image that a coordinating user desires. Additionally, some embodiments provide the coordinating user (typically a medical researcher or practicing physician who wants to collect medical image review data) with very strong control over the allowed inputs and the format of the data obtained. Further, some embodiments permit the coordinating user to provide instructions for how to accomplish the review within the review application itself. These and other features and benefits of the disclosed invention are set forth herein and shown and described in reference to the figures.

FIG. 1 is a flow diagram of a method 100 for creating a medical image review form template according to some embodiments. The review form template produced by method 100 may be used to generate review forms as shown and described below with respect to FIG. 3. Method 100 may be implemented using a system as shown and described below in reference to FIG. 7, for example.

Figure 7:
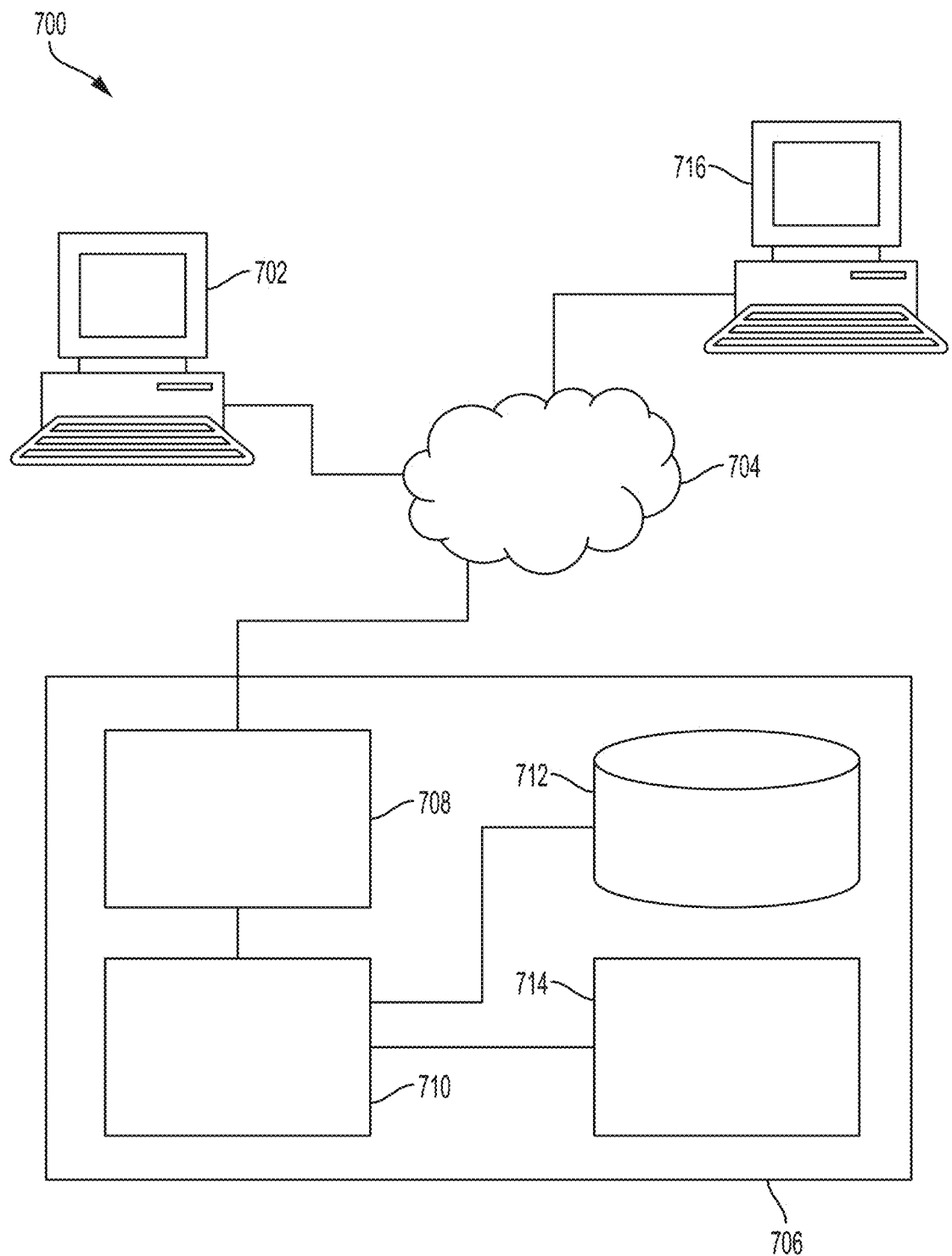
FIG. 7 is a schematic diagram of a system suitable for implementing methods according to some embodiments.

At block 102 of method 100, the central server (e.g., central server 706 of FIG. 7) provides a form template construction application to a coordinating user's computer (e.g., client computer 702 of FIG. 7). The application may be provided in a variety of ways. According to some embodiments, the application is provided over a network such as the internet. According to some such embodiments, the coordinating user may navigate a browser executing at the coordinating user's computer to a web page or other network resource (e.g., by entering a URL or clicking on a link), where the application may be downloaded. Alternately, the application may be provided as instructions on a non-transitory computer readable medium or media. Such media may be provided by sending through regular mail, for example. The form template construction application, when executing on a computer of a coordinating user, communicates with the centralized server computer, e.g., via application program interface (API), to effectuate the form template construction and other techniques shown and disclosed herein, as described presently.

At block 104 of method 100, the central server receives form template construction inputs from a computer of the coordinating user. In more detail, the coordinating user's computer executes the form template construction application, which provides an interface through which the coordinating user enters parameters that define the form template. The form template defines the forms that the reviewing users will use to enter their review data. The forms, in turn, may be configured by the form template construction application to include a series of prompts for the reviewing user's input. Whether image or metadata, the prompts may be designated by the coordinating user as either optional or mandatory for completion by the reviewing users. Prompts designated as mandatory may be visually distinguished from optional prompts, e.g., through the use of highlighting or other altered textual presentation.

A prompt may be either an image-prompt or a metadata-prompt. An image prompt instructs the reviewing user to annotate or select regions inside an image that meet specified criteria. A metadata prompt instructs the reviewing user to enter information about an image (e.g. whether the image contains evidence of metastasis, whether the image is of a patient who experienced a particular outcome or underwent a particular treatment, etc.). The coordinating user, using the form template construction application, may create any number of prompts, configuring each one to properly instruct the reviewing users as to the desired reviewing information.

Image prompts have different configuration options than metadata-prompts. An image prompt may include a configurable field for displaying instructions or a question. Additionally, an image prompt can be configured to limit how many regions can be selected by the recipient, and what shapes (ellipse, rectangle, freeform, etc.) the recipient may use to select the regions.

Figure 2:
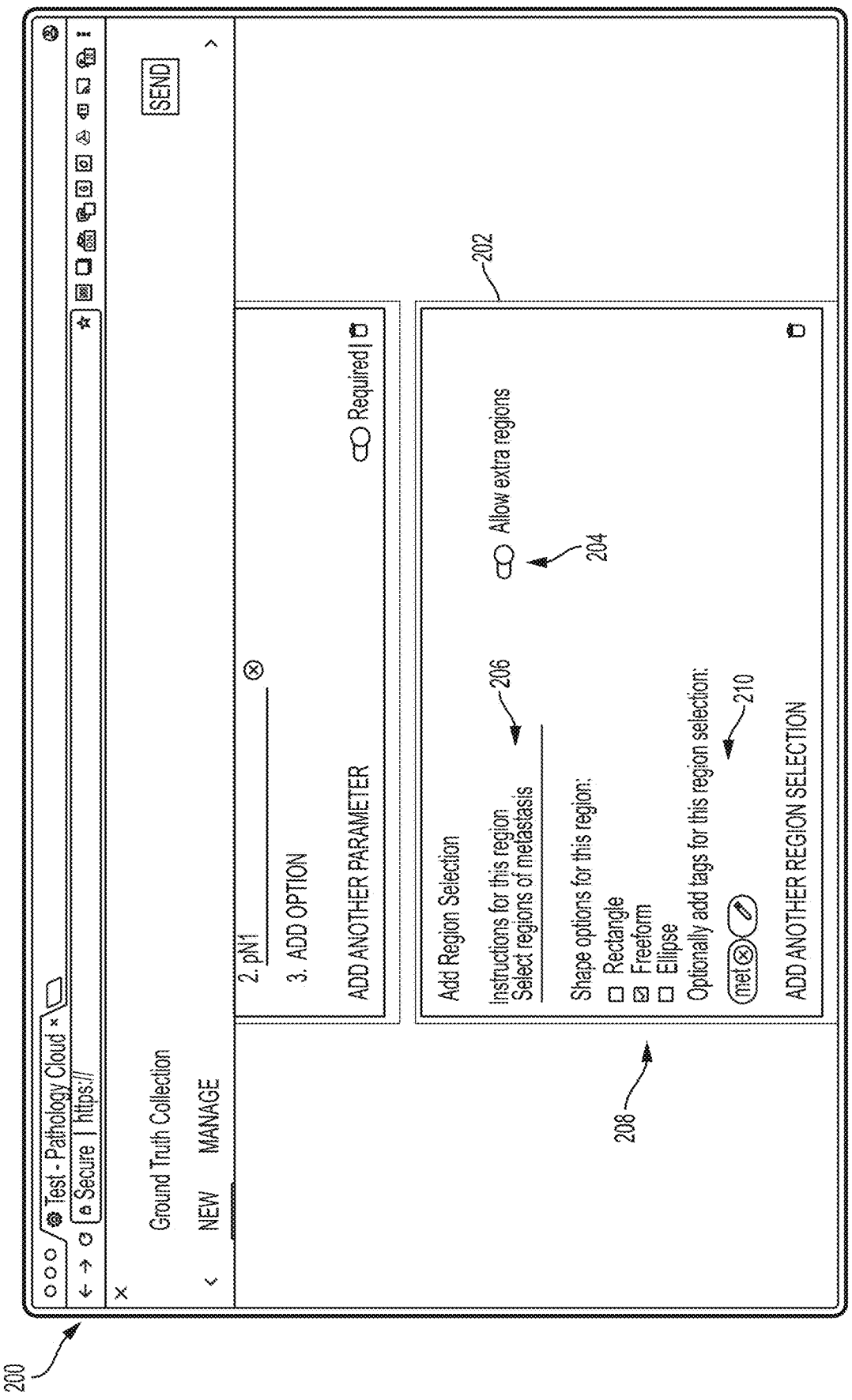
FIG. 2 is a screenshot of a portion of a form template construction application user interface for adding an image prompt according to some embodiments.

FIG. 2, for example, is a screenshot 200 of a portion of a form template construction application user interface for adding an image prompt according to some embodiments. As shown, screenshot 200 includes "add region selection" dialogue box 202. Dialogue box 202 includes a field 206 into which the coordinating user may enter instructions for the reviewing users to follow in completing the defined image prompt. Dialogue box 202 further includes check boxes 208 for specifying the type of shape with which the reviewing users may annotate the images. Dialogue box 202 further includes controls 210 for permitting the reviewing users to add tags to any annotated region. Dialogue box 202 further includes a virtual switch 204, which, when activated, permits a reviewing user to select additional regions in the images when reviewing them using a form defined by a form template generated in part using dialogue box 202.

Returning to the description of FIG. 1, metadata prompts have a configurable field for instructions or a question. Additionally, a metadata prompt can be configured to regulate the responses that the reviewing users can enter. The coordinating user may configure a metadata prompt to accept unrestricted text input, Boolean (true/false) input, numeric input, a predefined response out of a list of multiple predefined responses (multiple choice), or another input.

Thus, at block 104, the central server receives form template construction inputs from a coordinating user as conveyed by the form template construction application.

At block 106 of method 100, the central server creates or updates the form template. That is, if the inputs received at block 104 are the first inputs for a particular form template, then block 106 creates a new form template; otherwise, if the inputs received at block 106 are updates to an existing form template, then block 106 updates that template with data from the additional inputs. Thus, updates to the form template (including its constituent prompts) are sent over the network from the form template construction application of the coordinating user to the centralized server. A structured language such as XML or JSON may be used to describe the data structure either in transit or at rest.

At block 108, method 100 persists the form template at the central server. According to some embodiments, the central server persists the form template at every step of its creation, e.g., with each new received construction input of block 104. The form template may be persisted as a data structure in a language such as XML or JSON in persistent memory 712 of central server 706 of FIG. 7, for example.

At block 110, method 100 determines whether the form template construction process is finished. Method 100 may accomplish this by receiving an indication of completion from the client computer of the coordinating user that is executing the form template construction application. The coordinating user him- or herself may manipulate a virtual control, e.g., a button labeled "done", to initiate the completion. If the form template is not done at block 110, then the process loops back to block 104 to receive additional form template construction inputs. Otherwise, if the form template is complete at block 110, then method 100 branches to block 112, in which the form template is complete and the coordinating user is ready to obtain review data from expert reviewers using the newly-created from template.

Figure 3:
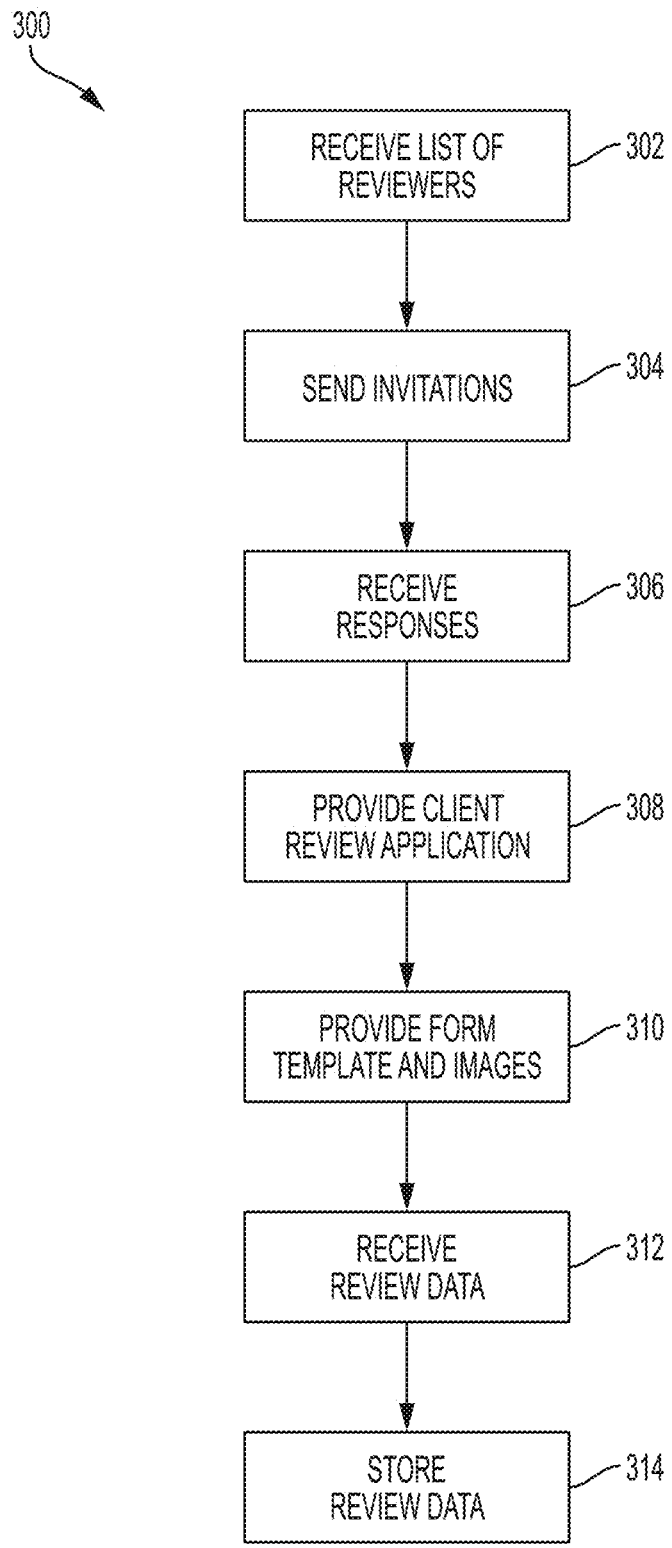
FIG. 3 is a flow diagram of a method for obtaining medical image review data according to some embodiments.

FIG. 3 is a flow diagram of a method 300 for obtaining medical image review data according to some embodiments. The form template produced by method 100 of FIG. 1 may be used to generate review forms and thereby obtain review data from reviewing users according to method 300. That is, the coordinating user may, using the form template construction application, send the survey to an arbitrary list of recipients for evaluation and completion. Method 300 may be implemented using a system as shown and described below in reference to FIG. 7, for example.

At block 302, method 300 receives a list of reviewing users. The coordinating user may enter a list of recipients, e.g., by selecting names or identifiers from a list, by entering email addresses, or by emailing using a batch email technique. Note that the list of reviewing users may be updated at any time. Once updated, the remainder of the process of method 300 may be completed for the newly added reviewing users.

At block 304, once the recipient reviewing users have been selected per block 302, and at the coordinating user's command, method 300 by way of the form template construction application sends a message containing the recipient list, e.g., via API, to the centralized server. The form template construction application may also send a reference to or identifier for the particular survey to send to the recipient reviewing users. The centralized server, upon receipt of that message, may record the recipients in its database system, and may send notifications via email or another medium to each recipient reviewing user.

Figure 4:
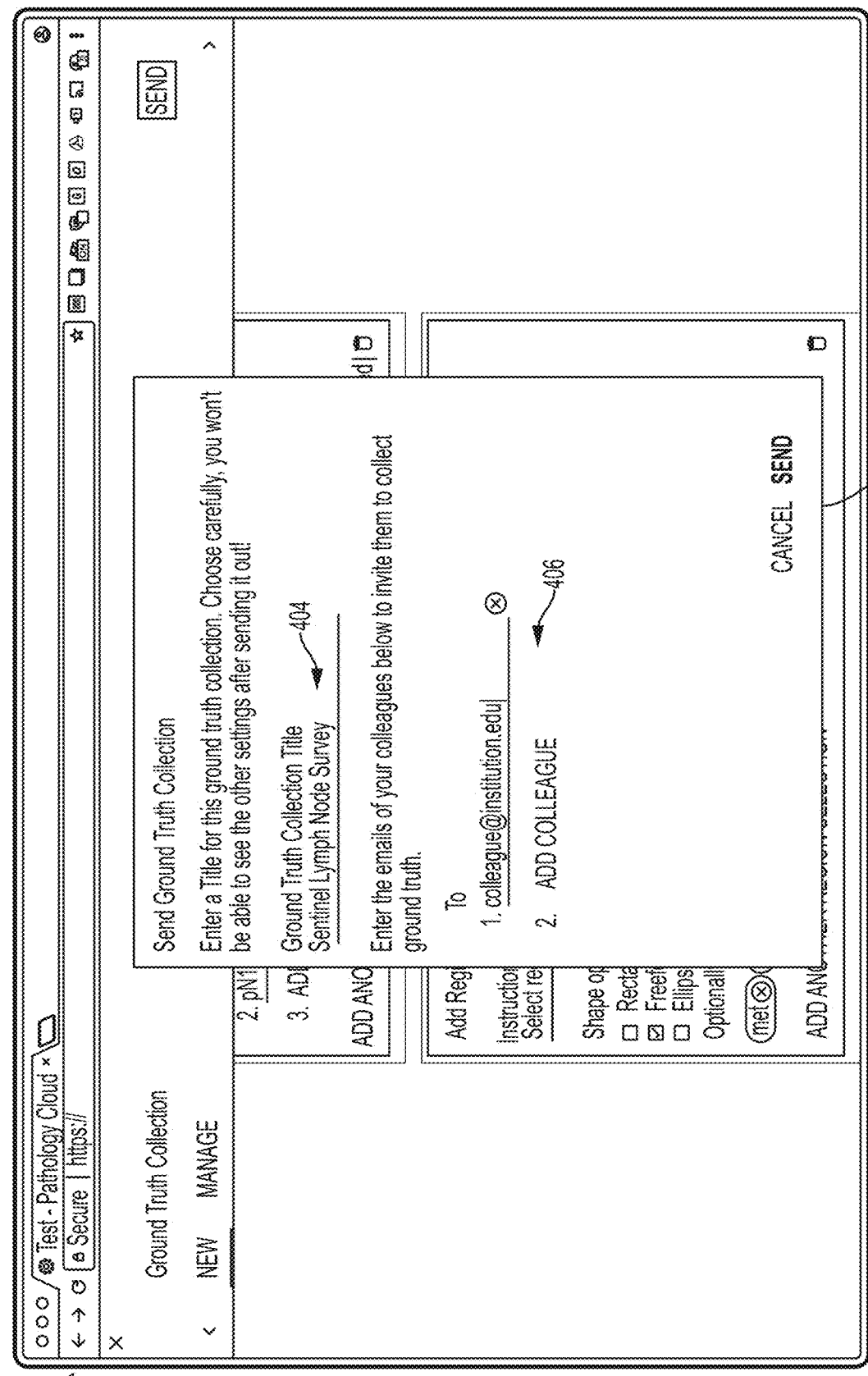
FIG. 4 is a screenshot of a portion of a reviewer list input interface according to some embodiments.

FIG. 4, for example, is a screenshot 400 of a portion of a reviewer list input interface according to some embodiments. As shown, screenshot 400 includes "send ground truth collection" dialogue box 402. Dialogue box 402 includes field 404 into which the coordinating user may enter a name for the form template and associated data collection effort. Dialogue box 402 also includes reproducible field 406 into which the coordinating user may enter email addresses of the desired reviewers. Dialogue box 402 also includes a button, which, when actuated, sends invitations to the appropriate reviewing users.

Returning to the description of FIG. 3, method 300 receives responses from the selected reviewing user recipients. The responses may be received in a variety of different manners. According to some embodiments, the responses are received as simple email messages. The form template construction application may parse such email messages to detect words such as "accept" or "decline". Alternately, the responses may be received by the form template construction application by way of an API, e.g., as triggered by buttons embedded in invitation emails.

At block 308, method 300 provides each of the reviewing users from whom affirmative responses were received with a review application. Note that the actions of this block can occur at any time prior to the actions of block 310. The review application may be provided in a variety of ways. According to some embodiments, the review application is provided over a network such as the internet. According to some such embodiments, the reviewing users may navigate a browser executing at their respective computers (e.g., such as client computer 716 of FIG. 7) to a web page or other network resource (e.g., by entering a URL or clicking on a link), where the review application may be downloaded. Alternately, the application may be provided as instructions on a non-transitory computer readable medium or media. Such media may be provided by sending through regular mail, for example. The review application, when executing on a computer of a reviewing user, communicates with the centralized server computer, e.g., via application program interface (API), to effectuate the review data gathering techniques shown and disclosed herein, as described presently.

At block 310, method 300 provides the form template and at least one image for review to the reviewing users. The actions of this block may be performed by the review applications executing on the various client machines of the reviewing users. The executing review applications may obtain the appropriate form template and images from the central server by retrieving them as needed. In more detail, the executing client applications may pull the appropriate form template from the central server at the beginning of the process, once the respective reviewing users respond affirmatively per block 306. The executing client applications may pull the images on an as-needed basis from the central server. Some embodiments employ a look-ahead technique, whereby they pull one or several images in advance of their review. Thus, such embodiments may pull one or more next images during a time period when the reviewing user is reviewing a current image.

At block 312, method 300 receives review data from the reviewing users. The review data may be received incrementally, e.g., upon completion of each image's review. The review data may be transmitted via API to the central server in an XML or JSON document, for example. At block 314, method 300 stores the review data in persistent memory.

At block 314, method 300 stores the received review data. The central server may retain a received structured XML or JSON document, and/or parse such a document to extract the information contained therein.

Figure 5:
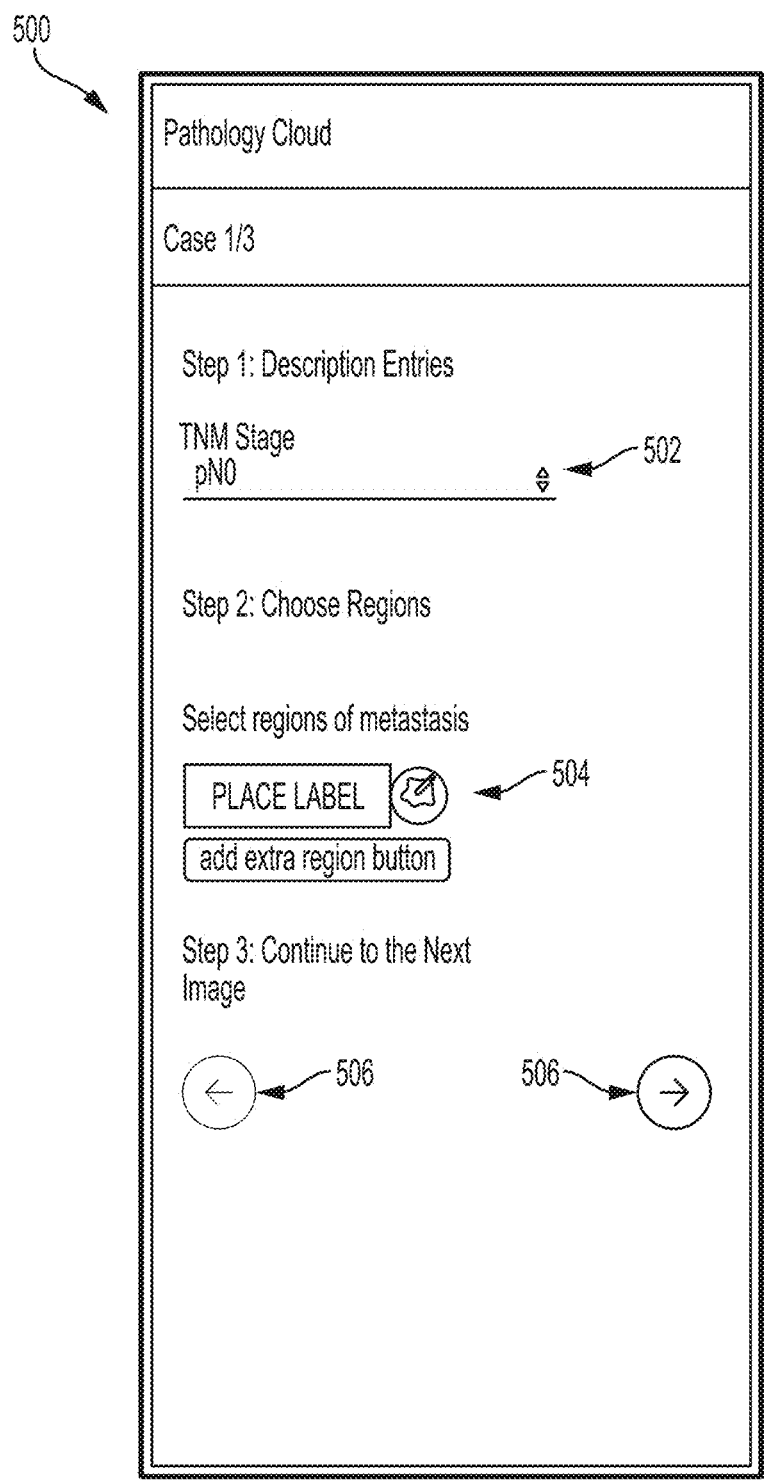
FIG. 5 is a screenshot of a portion of a medical image reviewer interface as seen by a reviewing user according to some embodiments.
Figure 6:
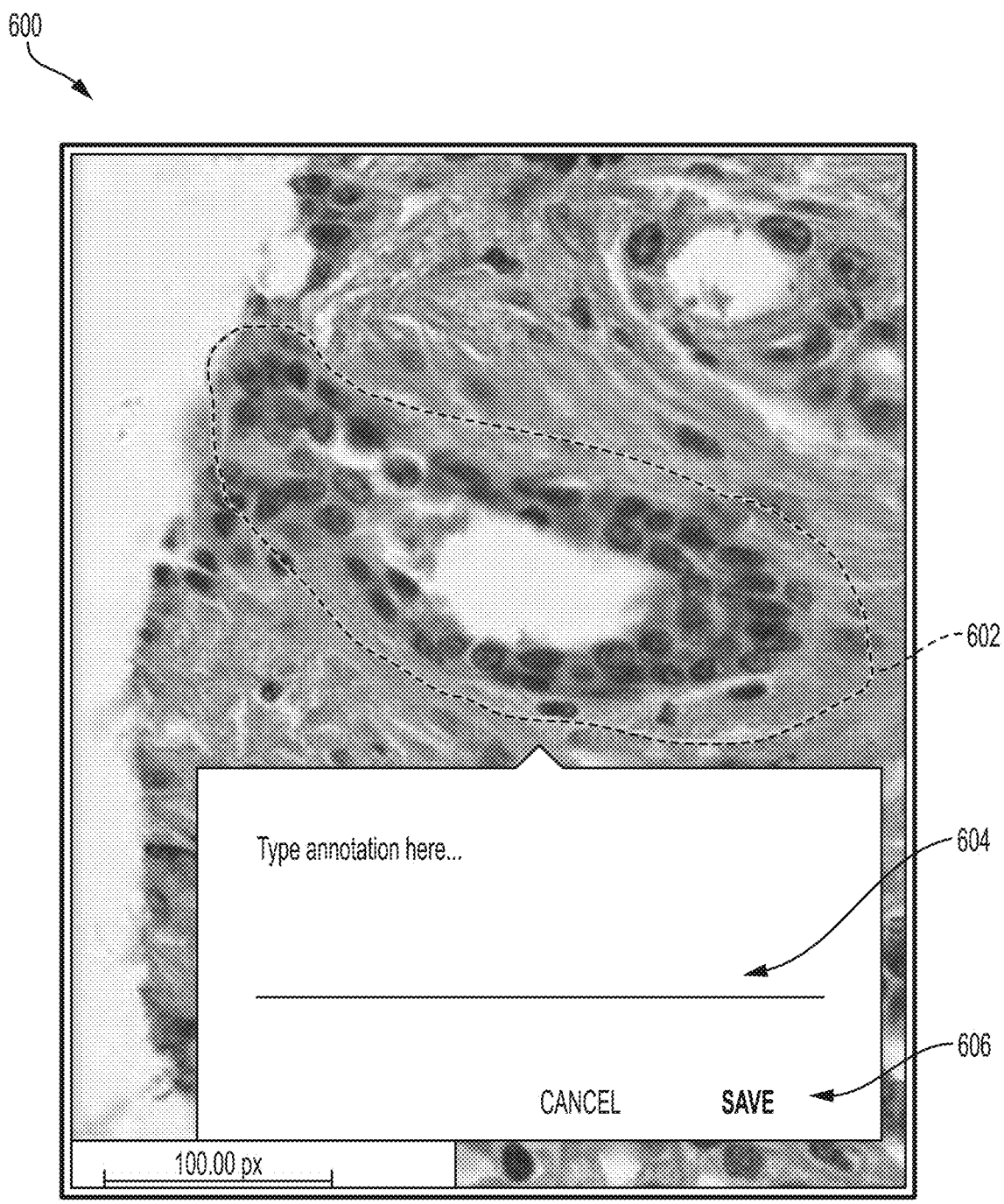
FIG. 6 is a screenshot of a portion of a medical image annotation window as seen by a reviewing user according to some embodiments.

The review data received and stored at the central server may include any of a variety of types. For example, the review data may include an identification of a region on an image and a corresponding diagnosis. FIGS. 5 and 6, described in detail below, depict several types of review data that may be obtained, as well as example form representations for obtaining it.

FIG. 5 is a screenshot 500 of a portion of a medical image reviewer interface as seen by a reviewing user according to some embodiments. The reviewer interface may exist in a virtual window separate from a virtual window in which the medical image under review is displayed. The reviewer interface includes drop-down menu 502 by which a reviewing user may select a diagnosis for a selected region. The reviewer interface also includes region selection controls 504, by which a reviewing user may use to draw a shape (e.g., circle, oval, square, rectangle, freeform) about a region on an image, place a label, and add additional region selection and labels. The reviewer interface also includes buttons 506 that the reviewing user may use to advance to the next image for review, or go back to the prior image. According to some embodiment, the advance button may be disabled until the reviewing user provides responses to all prompts that have been designated as mandatory rather than optional by the coordinating user. According to some embodiments, activating the advance button advances to the next unreviewed image.

FIG. 6 is a screenshot of a portion of a medical image annotation window 600 as seen by a reviewing user according to some embodiments. Window 600 depicts freeform shape 602, which a reviewing user drew about a region in the image using the review application (e.g., by way of region selection controls 504 of FIG. 5) to designate tissue with a property that the reviewing user can annotate by entering text in annotation field 604. Window 600 also includes a "save" button 606, by which the graphical and textual annotation may be saved.

Once obtained, the review data may be used for any of a variety of purposes. According to some embodiment, the review data is used for crowd-sourced (or individual) diagnoses. According to some embodiments, the review data is used as training data for a machine learning technique.

In more detail, some embodiment use the images and respective review data as training data (or "ground truths") for a machine learning technique. In such techniques, a set of labeled images are provided to a learning algorithm as training data. The learning algorithm is configured by the training data such that when input with a new unlabeled image for processing, it outputs an appropriate label. Suitable machine learning techniques as contemplated for use with disclosed embodiments include support vector machines, neural networks (e.g., convolutional, adaptive, etc.), and decision trees. Embodiments of the present invention may be used to generate a set of labeled images, used as training data, for such machine learning techniques.

For such embodiments, the training data may undergo stain normalization prior to use. Whole slide images may contain mass amounts of heterogeneity due to staining errors, tissue types, scanning variability, and/or naturally occurring entropy due to other human error in the tissue handling process. Without elimination of the stain variability, the heterogeneity of the stains may introduce bias to the machine learning model, and possibly even induce a bimodal stain vector color distribution. Stain normalization of the images may proceed as follows. First, the RGB-based images are converted to a perceptual-based color space, e.g., the LAB color space. Second, the resulting data is converted to a logarithmic cone space. Third, use a cross-section of naturally occurring images to decorrelate the color space axes in the logarithmic cone space. Finally, map this data to a color space defined by an achromatic color channel, a yellow-blue color channel, and a red-green color channel. The resulting images are stain normalized and suitable for use as training data for a machine learning technique.

FIG. 7 is a schematic diagram of a system 700 suitable for implementation of a method as shown and described, e.g., method 100 and/or 300. System 700 may be based around an electronic hardware internet central server computer 706 that includes one or more electronic processors 710, which may be communicatively coupled to the internet 704. System 700 includes network interface 708 to affect the communicative coupling to the internet 704, and, through internet 704, client computers 702, 716. According to some embodiments, the coordinating user operates client computer 702, which executes a form template construction application, and the reviewers operate other client computers, e.g., client computer 716, which execute copies of the review application. Network interface 708 may include a physical network interface, such as a network adapter. System 700 may be a special-purpose computer, adapted for reliability and high-bandwidth communications. Thus, system 700 may be embodied in a cluster of individual hardware server computers, for example. Processors 710 may be multi-core processors suitable for handling large amounts of information. Processors 710 are communicatively coupled to persistent memory 712, and may execute instructions stored thereon to effectuate the techniques disclosed herein on concert with client computer 702 and/or client computer 716 as shown and described in reference to FIGS. 1 and 3. Processors 710 are also communicatively coupled to volatile memory 714. Persistent memory 712 may be in a Redundant Array of Inexpensive Disk drives (RAID) configuration for added reliability, and volatile memory 714 may be or include Error-Correcting Code (ECC) memory hardware devices.

Various features and alternatives to the above-described embodiments are possible and contemplated. The review data may characterize a region of an image, an entire image, or a plurality of images. A reviewing user may tag a selected region with an on-image textual field. Any given input for a form may optionally contain the choice for a reviewing user to add an extra instance of the input field. When a reviewing user exits the review application or otherwise stops his or her review, the review data and location of termination may be persisted from the state the user left.

Certain examples described above can be performed in part using a computer application or program. The computer program can exist in a variety of forms, both active and inactive. For example, the computer program can exist as one or more software programs, software modules, or both, that can be comprised of program instructions in source code, object code, executable code or other formats, firmware program(s), or hardware description language (HDL) files. Any of the above can be embodied on a computer readable medium, which can include computer readable storage devices and media in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes.

Those skilled in the art will be able to make various modifications to the described examples without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A computer-implemented method of evaluating medical images, the method comprising:
   accessing an electronically stored plurality of medical images;
   providing to a computer of a coordinating user, by a server computer and over a computer network, a form template construction application, the form template construction application comprising a tool for creating on a form template at least one user control for designating a region on a medical image of the plurality of medical images, and a tool for creating on a form template at least one user input for receiving diagnosis data about a medical image of the plurality of medical images;
   receiving electronically at the server computer, from the computer of the coordinating user, form template construction inputs provided to the form template construction application by the coordinating user, the form template construction inputs comprising data representing at least one user control for designating a region on a medical image of the plurality of medical images, and data representing at least one user input for receiving diagnosis data about a medical image of the plurality of medical images;
   creating an electronic form template based on the form template construction inputs, the electronic form template specifying at least one user control for designating a region on a medical image of the plurality of medical images, and at least one user input for receiving diagnosis data about a medical image of the plurality of medical images;
   receiving electronically at the server computer, from the computer of the coordinating user, data representing a list of reviewing users;
   sending electronically over the computer network and by a server computer, to a computer of at least one reviewing user whose identity is on the list of reviewing users, an invitation to review the plurality of medical images;
   receiving an affirmative response to the invitation from the computer of the at least one reviewing user;
   providing electronically, by a server computer and over the computer network, a review application to the computer of the at least one reviewing user;
   providing electronically, by a server computer and over the computer network, to an executing instance of the review application on the computer of the at least one reviewing user, the form template and the plurality of medical images;
   receiving electronically by a server computer over the computer network, from the computer of the at least one reviewing user, and through the review application, review data for each of the plurality of electronically stored medical images representing inputs by the at least one reviewing user to a plurality of review forms derived from the form template, the review data representing at least one specified region on a medical image of the plurality of medical images and at least one diagnosis datum for a medical image of the plurality of medical images; and
   electronically storing the review data in persistent memory.

2. The method of claim 1, further comprising:
   training a machine learning component using the plurality of medical images and the review data;
   receiving a novel medical image;
   applying the machine learning component to the novel medical image; and
   obtaining a diagnosis for the novel medical image from the machine learning component.

3. The method of claim 2, further comprising applying stain normalization to the plurality of medical images prior to the training.

4. The method of claim 1, where the receiving electronically by a server computer over the computer network, from the computer of the at least one reviewing user, and through the review application, review data for each of the plurality of electronically stored medical images representing inputs by the at least one reviewing user to a plurality of review forms derived from the form template comprises:
   receiving multiple instances of partial review data sent automatically from the review application without reviewing user initiation; and
   persisting each of the multiple instances of partial review data in persistent memory.

5. The method of claim 1, where the form template specifies a sequence of prompts, the sequence of prompts comprising image selection prompts and image metadata prompts;
   where the image selection prompts comprise the at least one user control for designating a region on a medical image of the plurality of medical images; and
   where the image metadata prompts comprise the at least one user input for receiving diagnosis data about a medical image of the plurality of medical images.

6. The method of claim 5, where each prompt of the sequence of prompts comprises an instruction for responding to the prompt.

7. The method of claim 6, where each instruction comprises a designation of one of: completion mandatory or completion optional.

8. The method of claim 1, where:
   the at least one user control for designating a region on a medical image of the plurality of medical images comprise at least one of: a shape selector, or a number of selectable regions ceiling; and
   the at least one user input for receiving diagnosis data about a medical image of the plurality of medical images comprises at least one of: a freeform text input field, a Boolean input, a numeric input, or a multiple choice input.

9. The method of claim 1, where the plurality of medical images comprise whole-slide medical images.

10. The method of claim 1, where the review application is configured to display to the reviewing user each medical image of the plurality of medical images in sequence.

11. A system for evaluating medical images, the system comprising:
- at least one server computer communicatively coupled to a computer network and to an electronically stored plurality of medical images, the at least one server computer configured to provide to a computer of a coordinating user a form template construction application, the form template construction application comprising a tool for creating on a form template at least one user control for designating a region on a medical image of the plurality of medical images, and a tool for creating on a form template at least one user input for receiving diagnosis data about a medical image of the plurality of medical images;
- where the at least one server computer is further configured to receive electronically, from the computer of the coordinating user, form template construction inputs provided to the form template construction application by the coordinating user, the form template construction inputs comprising data representing at least one user control for designating a region on a medical image of the plurality of medical images, and data representing at least one user input for receiving diagnosis data about a medical image of the plurality of medical images;
- where the at least one server computer is further configured to create an electronic form template based on the form template construction inputs, the electronic form template specifying at least one user control for designating a region on a medical image of the plurality of medical images, and at least one user input for receiving diagnosis data about a medical image of the plurality of medical images;
- where the at least one server computer is further configured to receive electronically, from the computer of the coordinating user, data representing a list of reviewing users;
- where the at least one server computer is further configured to send electronically over the computer network, to a computer of at least one reviewing user whose identity is on the list of reviewing users, an invitation to review the plurality of medical images;
- where the at least one server computer is further configured to receive an affirmative response to the invitation from the computer of the at least one reviewing user;
- where the server computer is further configured to provide electronically, over the computer network, a review application to the computer of the at least one reviewing user;
- where the at least one server computer is further configured to provide electronically, over the computer network, to an executing instance of the review application on the computer of the at least one reviewing user, the form template and the plurality of medical images;
- where the at least one server computer is further configured to receive electronically, over the computer network, from the computer of the at least one reviewing user, and through the review application, review data for each of the plurality of electronically stored medical images representing inputs by the at least one reviewing user to a plurality of review forms derived from the form template, the review data representing at least one specified region on a medical image of the plurality of medical images and at least one diagnosis datum for a medical image of the plurality of medical images; and
- where the at least one server computer is further configured to electronically storing the review data in persistent memory.

12. The system of claim 11, further comprising:
- an electronic computer executing a machine learning component trained using the plurality of medical images and the review data, where the electronic computer is configured to receive a novel medical image, apply the machine learning component to the novel medical image, and provide a diagnosis for the novel medical image from the machine learning component.

13. The system of claim 12, where the electronic computer is further configured to apply stain normalization to the plurality of medical images prior to training the machine learning component.

14. The system of claim 11, where the at least one server computer is further configured to receive multiple instances of partial review data sent automatically from the review application without reviewing user initiation, and persist each of the multiple instances of partial review data in persistent memory.

15. The system of claim 11, where the form template specifies a sequence of prompts, the sequence of prompts comprising image selection prompts and image metadata prompts;
- where the image selection prompts comprise the at least one user control for designating a region on a medical image of the plurality of medical images; and
- where the image metadata prompts comprise the at least one user input for receiving diagnosis data about a medical image of the plurality of medical images.

16. The system of claim 15, where each prompt of the sequence of prompts comprises an instruction for responding to the prompt.

17. The system of claim 16, where each instruction comprises a designation of one of: completion mandatory or completion optional.

18. The system of claim 11, where:
- the at least one user control for designating a region on a medical image of the plurality of medical images comprise at least one of: a shape selector, or a number of selectable regions ceiling; and
- the at least one user input for receiving diagnosis data about a medical image of the plurality of medical images comprises at least one of: a freeform text input field, a Boolean input, a numeric input, or a multiple choice input.

19. The system of claim 11, where the plurality of medical images comprise whole-slide medical images.

20. The system of claim 11, where the review application is configured to display to the reviewing user each medical image of the plurality of medical images in sequence.

* * * * *